United States Patent
Okuba

(10) Patent No.: US 8,796,908 B2
(45) Date of Patent: Aug. 5, 2014

(54) PIEZOELECTRIC BODY, ULTRASOUND TRANSDUCER, MEDICAL ULTRASOUND DIAGNOSTIC SYSTEM, AND NONDESTRUCTIVE ULTRASOUND TEST SYSTEM

(75) Inventor: Tsuyoshi Okuba, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 306 days.

(21) Appl. No.: 13/383,879

(22) PCT Filed: Mar. 2, 2010

(86) PCT No.: PCT/JP2010/053287
§ 371 (c)(1),
(2), (4) Date: Jan. 13, 2012

(87) PCT Pub. No.: WO2011/010484
PCT Pub. Date: Jan. 27, 2011

(65) Prior Publication Data
US 2012/0116228 A1   May 10, 2012

(30) Foreign Application Priority Data

Jul. 22, 2009 (JP) .................................. 2009-171029
Aug. 11, 2009 (JP) .................................. 2009-186407

(51) Int. Cl.
| | | |
|---|---|---|
| H01L 41/18 | (2006.01) | |
| C04B 35/634 | (2006.01) | |
| C04B 35/80 | (2006.01) | |
| C04B 35/491 | (2006.01) | |
| H01L 41/37 | (2013.01) | |
| C04B 35/472 | (2006.01) | |
| C04B 35/626 | (2006.01) | |
| A61B 8/00 | (2006.01) | |
| H01L 41/187 | (2006.01) | |

(52) U.S. Cl.
CPC ........... *A61B 8/00* (2013.01); *C04B 2235/3251* (2013.01); *C04B 35/6342* (2013.01); *A61B 8/4405* (2013.01); *C04B 35/63416* (2013.01); *C04B 2235/3255* (2013.01); *C04B 35/803* (2013.01); *C04B 35/491* (2013.01); *C04B 2235/422* (2013.01); *C04B 2235/3206* (2013.01); *C04B 2235/441* (2013.01); *C04B 2235/526* (2013.01); *H01L 41/37* (2013.01); *C04B 35/6344* (2013.01); *C04B 2235/449* (2013.01); *C04B 2235/5288* (2013.01); *C04B 2235/5264* (2013.01); *C04B 2235/3284* (2013.01); *C04B 2235/6582* (2013.01); *H01L 41/1875* (2013.01); *C04B 35/472* (2013.01); *C04B 35/6264* (2013.01); *C04B 2235/80* (2013.01); *C04B 2235/652* (2013.01); *H01L 41/183* (2013.01)
USPC ......................................................... 310/358

(58) Field of Classification Search
CPC .............. H01L 41/187; H01L 41/1871; H01L 41/1873; H01L 41/1875; H01L 41/1876; H01L 41/1878; H01L 41/16; H01L 41/18; H01L 41/183; C04B 35/472; C04B 35/491
USPC ......................................................... 310/358
See application file for complete search history.

(56) References Cited

FOREIGN PATENT DOCUMENTS

| JP | 2000-272964 | 10/2000 |
|---|---|---|
| JP | 2002-246670 | 8/2002 |
| JP | 2002-299063 | 10/2002 |
| JP | 2005-139064 | 6/2005 |
| JP | 2006-269391 | 10/2006 |

*Primary Examiner* — Derek Rosenau
(74) *Attorney, Agent, or Firm* — Lucas & Mercanti, LLP

(57) ABSTRACT

Disclosed is a piezoelectric body having both broad band property and improved piezoelectricity, which can be suitably used for a sensor, an actuator, an ultrasound transducer and the like. The piezoelectric body is featured in that (a) it comprises a laminate structure which is represented by the following general formula,

* 
* repetition of the unit layer
* 
* unit layer

General formula $$G_2MX_4$$

wherein G represents an organic onium, M represents an element of Group IV or a transition metal, and X represents Cl, Br or I, the organic onium G and an inorganic phase $MX_4$ being alternately superposed on each other in the form of layers; or in that (b) it comprises a composite of a graphene structure and a perovskite structure, the graphene structure being composed of aggregate particles with an average particle size of not more than 200 nm.

7 Claims, 3 Drawing Sheets

$d = 1/2 \times c \times t$ (d: THICKNESS
c: SONIC SPEED
t: TRAVEL TIME)

PIEZOELECTRIC BODY, ULTRASOUND TRANSDUCER, MEDICAL ULTRASOUND DIAGNOSTIC SYSTEM, AND NONDESTRUCTIVE ULTRASOUND TEST SYSTEM

CROSS REFERENCE TO RELATED APPLICATION

This Application is a 371 of PCT/JP2010/053287 filed on Mar. 2, 2010 which, in turn, claimed the priorities of Japanese Patent Application Nos. 2009-171029 filed on Jul. 22, 2009 and JP 2009-186407 filed on Aug. 11, 2009, all three Applications are incorporated by reference herein.

TECHNICAL FIELD

This invention relates to a piezoelectric body with a high piezoelectricity and abroad band property suitably used for a sensor, an actuator, an ultrasound transducer, and the like, and to an ultrasound transducer, a medical ultrasound diagnostic system and a nondestructive ultrasound test system, each employing the piezoelectric body.

TECHNICAL BACKGROUND

Hitherto, a piezoelectric body, which is composed of materials such as inorganic ceramics or an organic polymer, has been suitably used for a sensor, an actuator, an ultrasound transducer, and the like.

As the inorganic ceramics, there are well known a $PbZrO_3$/$PbTiO_3$ solid solution (PZT), a $Pb(Mg_{1/3}Nb_{2/3})O_3$/$PbTiO_3$ solid solution (PMN-PT), a $Pb(Zn_{1/3}Nb_{2/3})O_3$/$PbTiO_3$ solid solution (PZN-PT), and the like. A piezoelectric constant $d_{33}$ characterizing a piezoelectric body is an index converting force to electric charge. The typical $d_{33}$ values of the above-described ceramics are 550, 2820 and 2000 (the unit is pC/N), respectively, which are considerably higher as compared with those of polymers described later.

As a representative example of the polymers, there is mentioned vinylidene fluoride-trifluoroethylene copolymer (P(VDF-3FE)) whose $d_{33}$ is about 17. In order to improve this property in the polymers, there have been hitherto studied organic polymer materials such as a kneaded mixture of P(VDF-3 FE)) with polyurethane or silicone (U.S. Pat. No. 6,689,288), a kneaded mixture of polyvinylidene fluoride with nylon (US patent Publication No. 2002/0166620), polybutadiene, a poly(N,N-methylenebisacrylamide-styrene) copolymer (Japanese Patent O.P.I. Publication No. 2006-049418), a high magnetic field application molded product of poly(γ-benzyl-L-glutamate) (Japanese Patent O.P.I. Publication No. 2005-217111), a polyurea obtained by vapor deposition polymerization of methane diisocyanate and diaminofluorene (Atsushi Kubono, Masashi Mural and Shigeru Tasaka, "High Piezoelectric Activity in Nonpoled Thin Films Prepared by Vapor Deposition Polymerization", Japanese Journal of Applied Physics, Japan, The Japan Society of Applied Physics, Jul. 11, 2008, Vol. 47, 7, p. 5553-5557), an electret in which air bubbles are incorporated in a tetrafluoroethylene-hexafluoropropylene copolymer (Japanese Patent O.P.I. Publication No. 2007-231077) and the like; and materials such as a PZT-siloxane-poly(meth)acrylate composite (Japanese Patent O.P.I. Publication No. 2002-185054), a composite of polylactic acid with calcium phosphate or montmorillonite (Japanese Patent O.P.I. Publication No. 2005-213376) and the like. However, a satisfactory performance has not yet been obtained.

In recent years, as a property required in addition to $D_{33}$ described above when a piezoelectric body is applied to a transducer or a sensor, there is a frequency bandwidth in which the piezoelectricity is developed, and it is demanded that the piezoelectric body can be utilized in a broad frequency bandwidth.

When a piezoelectric body having a broad bandwidth is used, for example, in a medical ultrasound diagnostic system, a single piezoelectric body enables both transmission of a low frequency ultrasound capable of being transmitted to deeper diagnosis domain and reception of high spatial resolution information in which high order harmonic components are superposed by non-linear propagation. Hitherto, no piezoelectric body with a broad band property has been found which can realize such a performance, and a high sensitive piezoelectric body for transmission and a high sensitive piezoelectric body for reception have been separately employed according to the respective frequency band.

As the index of the bandwidth (-6 dB bandwidth), there is a ratio of a frequency providing the highest output and the difference between the maximum frequency and the minimum frequency where the highest output is reduced to half (-6 dB attenuation).

The ratio in the ceramics as described above is in the range of from 10 to 70%, and the ratio in the known polymer materials is in the range of from 80 to 400%.

As is apparent from the aforementioned, there is a contradictory relationship between the bandwidth and $d_{33}$, and it is extremely difficult to enhance both properties simultaneously. When a material in which both properties are simultaneously enhanced is used in a transducer, a medical ultrasound diagnostic system and a nondestructive ultrasound test system, each employing the transducer, provide diagnosis with high precision and detection with high accuracy, respectively.

In order to solve this problem, composites of PZT and polymer materials have been developed, and among these, a 1-3 composite is representative in which the longitudinal of the PZT prism is oriented in the vibration direction (see Non-Patent Document 1). The $d_{33}$ and bandwidth of this composite is in the range of from 50 to 200 pC/N and in the range of from 50 to 150%, respectively, although the $d_{33}$ and bandwidth depend mainly on the configuration of the PZT prism (see Non-Patent Document 2).

Proposed is an attempt which employs, instead of PZT, a single crystal ($d_{33}$=1200 cP/N) of $[Pb(Mg_{1/3})(Nb_{2/3})O_3]_{0.68}$ $[PbTiO_3]_{0.32}$ which enhances $d_{33}$ (see Patent Document 1). However, the $d_{33}$ of the resulting 1-3 composite is 120 pC/N, and the property of the single crystal cannot be effectively utilized.

A composite material obtained by calcining, at a low temperature, fullurene and PZT prepared according to a sol-gel method is known (see Patent Document 2). However, the composite material, containing fullurene dispersion particles exceeding 200 nm and having a fullurene content of 10% by volume, is far lower in the piezoelectricity than PZT, and hardly broadens the bandwidth.

As the bandwidth range of the frequency used is broadened, there is high demand to further improve these properties.

Examples, in which halide based perovskite compounds in the form of layers are applied to an electroluminescence element and the like, have been hitherto known (see, for example, Patent Document 3), however, it is unknown that these are used as a piezoelectric body.

PRIOR ART LITERATURE

Patent Literature

Patent Document 1: Japanese Patent O.P.I. Publication No. 2005-139064
Patent Document 2: Japanese Patent O.P.I. Publication No. 2000-272964
Patent Document 3: Japanese Patent O.P.I. Publication No. 2002-299063

NON-PATENT LITERATURE

Non-Patent Document 1: Hisao Sakano, "Atsuden Ceramics: Polymer Composite", Solid Physics, Japan, Agne Gijutsu Center Co., Ltd., Published on Aug. 15, 1998, Vol. 23, 8, P. 133-143.

Non-Patent Document 2: Kazuo Nakamae, Yoshihiro Hirata, Hirofumi Mizobuchi, Akishiro Hashimoto, Hiroshi Takada, "Kobunkaino, Kotaiiki Fukugoatsuden Zairyo no Kaihatsu", SEI Technical Review, Japan, Sumitomo Electric Industries, Ltd., Vol. 163, P. 48-52 (September 2003).

DISCLOSURE OF THE INVENTION

Problems to be Solved by the Invention

The present invention has been made in view of the above. An object of the invention is to provide a piezoelectric body with both broad band property and improved piezoelectricity, which can be suitably used for a sensor, an actuator, an ultrasound transducer, and the like.

Means for Solving the Above Problems

The above object of the invention can be attained by any one of the following constitutions:

1. A piezoelectric body featured in that (a) it comprises a laminate structure which is represented by the following general formula,
General formula $$G_2MX_4$$

wherein G represents an organic onium, M represents an element of Group IV or a transition metal, and X represents Cl, Br or I, the organic onium G and an inorganic phase $MX_4$ being alternately superposed on each other in the form of layers, or in that (b) it comprises a composite of a graphene structure and a perovskite structure, the graphene structure being composed of aggregate particles with an average particle size of not more than 200 nm.

2. The piezoelectric body of item 1 above, featured in that in the general formula in (a), the organic onium is an organic ammonium, an organic phosphonium, an organic sulfonium or an organic oxonium.

3. The piezoelectric body of item 1 or 2 above, featured in that in the general formula in (a), the M is Cd, Cu, Fe, Mn, Pd or Pb.

4. The piezoelectric body of any one of items 1 through 3 above, featured in that the laminate structure in (a) is an organic perovskite in the form of layers.

5. The piezoelectric element of item 1 above, featured in that the graphene structure in (b) is a carbon nanotube with a diameter of not more than 60 nm or fullerene.

6. The piezoelectric body of item 1 or 5 above, featured in that the perovskite structure in (b) comprises lead, and is a solid solution, polycrystal or single crystal of a compound having one or more kinds of chemical formulae.

7. The piezoelectric body of any one of items 1, 5 and 6 above, featured in that the composite in (b) has a volume resistivity of from $10^3$ to $10^{12}$ Ω.m.

8. An ultrasound transducer featured in that it employs the piezoelectric body of any one of items 1 through 7 above.

9. A medical ultrasound diagnostic system featured in that it employs the ultrasound transducer of item 8 above.

10. A nondestructive ultrasound test system featured in that it employs the ultrasound transducer of item 8 above.

Effects of the Invention

The above constitutions of the invention can provide a piezoelectric body with a broad band property and improved piezoelectricity, which can be suitably used for a sensor, an actuator, an ultrasound transducer and the like.

PREFERRED EMBODIMENTS FOR CARRYING OUT THE INVENTION

Next, the preferred embodiments of the invention will be explained in detail.

Figure 4:
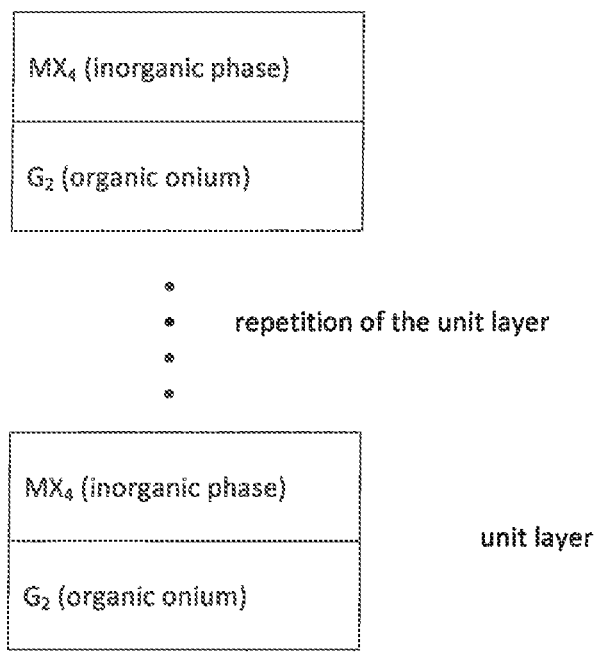
FIG. 4 shows alternating, superposed laminate structure of the organic onium G and an inorganic phase $MX_4$.

The piezoelectric body as the first embodiment of the invention is featured in that (a) it has a laminate structure in which an inorganic crystal, preferably an inorganic cubic crystal composed of $MX_4$ (in which M represents an element of Group IV or a transition metal, and X represents Cl, Br, or I) and two molecules ($G_2$) of an organic onium are alternately superposed on each other in the form of layers. Such a structure is shown in FIG. 4. The former inorganic cubic crystal has a valence of −2 per molecule, and the latter onium has a valence of +1 per molecule, and both are combined with each other through an ionic bond, forming a perovskite structure in which a laminate structure formed through the ionic bond is regularly maintained over a long distance.

When this structure is subjected to polarization treatment in a high electric field of from 1 to 100 MV/m, a central atom M is displaced from four Xs positioned on the verteces of the regular octahedron, whereby polarization occurs and piezoelectric properties are developed.

The element of M in the inorganic cubic crystal, which combines with the onium to form a layered ionic bond, is preferably an element of Group IV or a transition metal, and more preferably an element selected from Cd, Cu, Fe, Mn, Pd and Pb. X is restricted to a halogen atom such as Cl, Br or I.

When M is an element of Group IV or a transition metal, it combines with the X (halogen) to easily form a cubic crystal. When X is a halogen, it combines with an organic onium to form an ion pair, which makes it easy to obtain an objective organic layered perovskite.

A degree of polarization depends mainly on bulkiness of a substituent and ionic strength of the organic onium. When the substituent is bulkier and the ionic strength is higher, the degree of polarization is higher, exhibiting a higher piezoelectric strain constant $d_{33}$. Herein, $d_{33}$ shows elongation and contraction in the direction perpendicular to the electrode surface (in the thickness direction of the electrode). The displacement in the thickness direction is a product of $d_{33}$ and the voltage) is exhibited. Further, the piezoelectric body of the invention enables broadening of a band on account of a low Q factor (rapid damping) derived from the organic onium, and therefore, the piezoelectric body of the invention has a configuration useful to enhance both $d_{33}$ property and a broad band property, simultaneously. Owing to the broad band property, the piezoelectric body of the invention can provide a high sensitive transducer having a high spatial resolution capability and a high sensitivity to a high order higher harmonic wave.

The preferred chemical structure of the onium is ammonium, phosphonium, sulfonium or oxonium each having as a side chain, $C_nH_{2n+1}$ (n is an integer of firm 2 to 17), $ArC_nH_{2n}$, (Ar represents phenyl, a condensed aromatic group, a heterocyclic group or a derivative thereof and n is an integer of 1 to 17), $ALC_nH_{2n}$ (AL represents an alicyclic hydrocarbon group, a condensed alicyclic hydrocarbon group or a derivative thereof, and n is an integer of 1 to 17), a polymerizable group having an ethenyl group or an ethynyl group or a polymer as the derivative.

Examples of the onium preferably used in the invention will be shown below, but the present invention is not specifically limited thereto.

1. Trioctyl methyl ammonium
2. Triphenyl-n-butyl ammonium
3. Bis(2-bicyclo-2,2,1-heptyl)-3-p-tolylpropyl sulfonium
4. Trimethyl oxonium The piezoelectric body as the second embodiment of the invention comprises (b) a composite of a graphene structure and a perovskite structure, the graphene structure being composed of aggregate particles with an average particle size of not more than 200 nm. The graphene contributes significantly to scattering a sound wave traveling through a pure perovskite and lowering a Q factor, and therefore, is effective in broadening a frequency band range exhibiting a piezoelectricity. To the contrary, the graphene is a substance which does not have a piezoelectricity. However, the requisite amount thereof is 10% by volume or less, and preferably 0.5% by volume or less and 0.01% by volume or more. Such an amount of the graphene hardly impairs the piezoelectricity of the perovskite. In order to exert such a band broadening effect in such a low graphene content, it is necessary that the both interact with each other in a lattice level, and therefore, a composite comprising macro aggregate particles with an average particle diameter exceeding 200 nm hardly exhibits the band broadening effect. Accordingly, it is necessary that the composite be one in which the both with a particle size of not more than 200 nm are uniformly mixed. It has been found that the p electrons of the graphene with this particle size coordinate with the metal constituting B site of the perovskite, and even a slight content of the graphene effectively causes the sound wave scattering as described above.

<(b) Measurement of Aggregate Particles of Graphene Structure in the Composite>

The piezoelectric body of the invention comprises a composite of a graphene structure and a perovskite structure, the graphene structure being composed of aggregate particles with an average particle size of not more than 200 nm. The average particle size of the aggregate particles of the graphene structure can be measured employing an ultra low accelerating voltage scanning electron microscope equipped with a dispersion type X ray spectrometer, for example, ULTRA 55 produced by Zeiss Co., Ltd. In the invention, the average particle size of the aggregate particles of the graphene structure refers to a sphere-converted volume based average particle size of 100 or more particles in one electron microscope field of view.

Examples of a substance with a graphene structure effective for the interaction as described above include fullerenes such as C60 or C70; single-wall carbon nanotubes; multi-wall carbon nanotubes with an outermost diameter of not more than 60 nm; and graphite partially having amorphous phase. These graphites coordinate with a metal constituting a perovskite as described above, and strongly interact with preferably a perovskite comprising lead, and its effect is that band broadening is developed in a smaller content of the graphene. Preferred examples of the perovskite include a single substance, a solid solution, a single crystal and a polycrystal of $PbTiO_3$, $PbZrO_3$, $Pb(Mg_{1/3}Nb_{2/3})O_3$, $Pb(Zn_{1/3}Nb_{2/3})O_3$ or $A_2PbX_4$ (in which A is ammonium, and X is halogen).

<Manufacture of Ultrasound Transducer>

Next, manufacture of an ultrasound transducer employing the piezoelectric body of the invention will be explained.

The piezoelectric body of the invention can cut into an array comprising a plurality of piezoelectric elements through a conventional processor such as a diamond cutter in order to obtain an intended beam form of a radiation ultrasound. An electrode being provided on a flexible print substrate, each element enables any arbitrary beam forming by driving transmission and reception of an ultrasound by a programmed computer. In order to further improve an acoustic performance, the piezoelectric body of the invention, being laminated with a packing material absorbing an ultrasound, a matching material preventing reflection of an ultrasound, an acoustic lens for bringing an ultrasound into focus and the like, can be employed as a laminate structure. This ultrasound transducer may be subjected to water-proof treatment such as parylene coating or the like, so that it can be employed in water or under high humidity conditions. The thus obtained ultrasound transducer can be suitably applied to a medical ultrasound diagnostic system or a nondestructive ultrasound test system.

(Preparation of Piezoelectric Body)

According to various methods, the piezoelectric body of the invention can be prepared employing as the main components, the inorganic component $MX_4$ and the organic onium G in the above (a). For example, when lead halide is employed as the inorganic component, the element is prepared as follows. An organic onium salt and lead halide in a stoichiometrically equivalent amount are mixed and reacted in a solvent to produce $G_2MX_4$, and the resulting $G_2MX_4$ is isolated and dissolved in a coating solvent to prepare a coating solution, and the coating solution is coated on an appropriate substrate employing a solvent cast method, a spin coating method or a dip coating method, and dried to remove the coating solvent. Thus, a piezoelectric body precursor film is obtained.

As a solvent used for the above reaction or coating, there is mentioned an aprotic solvent, for example, an amide solvent such as dimethyl sulfoxide (DMSO), dimethylformamide (DMF), dimethyl acetamide or N-methylpyrrolidone; tetrahydrofuran; acetone; methyl ethyl ketone or toluene. When $G_2MX_4$ produced in the above has a desired purity, the reaction solution can be coated on a substrate without isolating $G_2MX_4$ to form the film. When the organic onium has a polymerizable group, it can be polymerized by heating, UV irradiation or radiation ray irradiation.

Next, a preparation method of the piezoelectric body in the above (b), which comprises a composite of a graphene structure and a perovskite structure, the graphene structure being composed of aggregate particles with an average particle size of not more than 200 nm, will be explained.

When fullurene is employed as the graphene, the toluene solution thereof is preferably used in order to prepare nano-sized particles. When perovskite pulverized to a particle size of from 5 to 100 nm is used, its alcohol slurry is mixed with a fullerene toluene solution to give the prescribed content. The resulting mixture solution is coated on a substrate, dried to remove the solvent, and then calcined at 1200° C. under an argon atmosphere, thereby obtaining a piezoelectric body precursor in the invention.

Further, when perovskite prepared according to a chemical solution method is used, a perovskite graphene composite with nano-sized particles can be easily prepared.

Next, an embodiment employing PZT will be explained.

Specifically, when PZT (a solid solution of $PbTiO_3$/$PbZrO_3$) is used, titanium tetraalkoxide and zirconium tetraalkoxide are added to an anhydrous lead acetate solution, and heated while stirring to be subjected to polycondensation. The reaction temperature is from 50 to 150° C., and the reaction period of time is from 1 to 20 hours. These reaction conditions are appropriately adjusted to give the possible highest degree of polycondensation. The resulting polycondensate solution is mixed with the above-described fullurene solution in a prescribed amount, and optionally diluted with a solvent such as alcohol to adjust so that the viscosity of a uniform coating solution to be used later to form a film is suitable to coat. The resulting mixture solution is coated on a substrate according to a spin coating method, a dip coating method or a cast coating method and air dried at room temperature for around two hours. The resulting film on the substrate is calcined in air at a temperature of from 70 to 120° C. for one to four hours and further at 350° C. for thirty minutes, and then heat treated at 550° C. for one to two hours and further at a temperature of from 900 to 1200° C. for four hours under an argon atmosphere having an oxygen concentration of not more than 5 ppm. Thus, the piezoelectric body precursor in the invention is prepared.

When the carbon nanotubes are used, a dispersion solution comprised of the alcohol slurry of perovskite pulverized to a particle size of from 5 to 100 nm as described above and single layered or multilayered carbon nanotubes is used. This uniform dispersion solution is coated on a substrate, dried to remove the solvent, and then calcined at 1200° C. under an argon atmosphere, thereby obtaining the piezoelectric body precursor in the invention.

When the carbon nanotubes are difficult to disperse, a dispersion auxiliary such as a surfactant may be employed in an amount of less than 0.5% by mass based on the carbon nanotube content. As another dispersion method, carbon nanotubes are produced in the perovskite particles, thereby obtaining a composite thereof in the nano level.

Next, another embodiment employing PZT will be explained.

Ferrocene is added in a prescribed amount to the polycondensate solution prepared according to the chemical solution method as described above to obtain a uniform solution. The amount of the carbon nanotubes produced depends on the amount of ferrocene used, and is adjusted to be preferably less than 0.2% based on the total perovskite amount. The resulting solution is coated on a tungsten carbide substrate and air dried to form a film. The resulting film on the substrate is heat treated at a temperature of from 70 to 120° C. for one to four hours and further at a temperature of from 900 to 1200° C. for four hours in air. Thereafter, the heat treated film is heated at a temperature of from 1500 to 1800° C. under a hydrogen and toluene vapor atmosphere to obtain a composite in which the carbon nanotubes grow. The resulting composite is calcined, under an atmosphere of inert gas such as argon having an oxygen concentration of not more than 5 ppm, at a temperature of not lower than 1000° C., preferably not lower than 2000° C., and more preferably not lower than 3000° C. for from 0.5 to 5 minutes. Thus, the piezoelectric body precursor in the invention is prepared.

The piezoelectric body precursors obtained according to the above-described methods are subjected to polarization treatment due to application of electric field, thereby obtaining the piezoelectric body of the invention.

In the manufacturing method of the ultrasound transducer of the invention such as an ultrasound oscillator, it is preferred that polarization treatment is carried out before an electrode, which is to be formed on both sides of the piezoelectric body film, is formed, after an electrode has been formed only on one side of the piezoelectric body film, or after an electrode has been formed on both sides of the piezoelectric body film. Further, it is preferred that the polarization treatment is voltage application treatment.

When the electric shock is periodically given to a piezoelectric body, electric current occurs. When a high frequency alternating current is applied to the piezoelectric body, the piezoelectric body repeatedly elongates and shrinks in accordance with the change, whereby a density of air around the piezoelectric body periodically varies so that vibration (ultrasound) generates. Thus, the ultrasound is generated. While when an ultrasound is applied to the piezoelectric body to give a periodically repeated mechanical stimulus (acoustic wave), electric current occurs. A transducer is an element having a function capable of converting a certain stimulus to an electric stimulus or an electric stimulus to a certain stimulus.

The ultrasound oscillator as described later is therefore an ultrasound transducer. An ultrasound probe equipped with an ultrasound oscillator for reception and transmission or an ultrasound probe equipped with an ultrasound oscillator for reception or transmission comprised of a single piezoelectric body is also an ultrasound transducer.

(Substrate)

The substrate used is selected according to usage of the organic piezoelectric body film in the invention. As the substrate in the invention there can be used a plate or film of a plastic such as polyimide, polyamide, polyimideamide, polyethylene terephthalate (PET), polyethylene naphthalate (PEN), polymethyl methacrylate (PMMA), a polycarbonate resin, or a cycloolefin polymer. The substrate may be those in which the surface of these materials is covered with aluminum, gold, copper, magnesium, or silicon. The substrate may be a plate or film of aluminum, gold, copper, magnesium, silicon or a single crystal of a halide of rare earth element. In the invention, the substrate may not be used.

(Ultrasound Oscillator)

The ultrasound oscillator of the invention is featured in that it employs a piezoelectric body film formed by the piezoelectric body of the invention. Generally, an ultrasound oscillator has a structure that a layer (or film) formed from a piezoelectric material in the form of a film (also referred to as a piezoelectric film, a piezoelectric body film or a piezoelectric body layer) is inserted between a pair of electrodes. A plurality of ultrasound oscillators are arranged, for example, one dimensionally, thereby obtaining an ultrasound probe.

When a specific number of oscillators in the longitudinal direction of the plurality of ultrasound oscillators arranged are set to have an opening and driven, the oscillators irradiate the site to be examined in an examinee with convergent ultrasound beams, receive the ultrasound reflection echo reflected from the site and convert the echo to an electric signal.

<Electrode>

The ultrasound oscillator employing the piezoelectric body of the invention is one which is manufactured by forming an electrode on one or both sides of a piezoelectric body film (layer), and subjecting the piezoelectric body film to polarization treatment. In order to manufacture an ultrasound oscillator employing an organic piezoelectric body material, the electrode on the first surface employed for polarization treatment may be employed. The electrode is formed from electrode materials comprised mainly of gold (Au), platinum (Pt), silver (Ag), palladium (Pd), copper (Cu), nickel (Ni) or tin (Sn).

In the formation of the electrode, a layer of a metal such as titanium (Ti) or chromium (Cr) is formed according to a sputtering method as an under layer to obtain a thickness of from 0.02 to 1.0 μm, and then, metal materials composed mainly of the metal elements described above or metal materials composed of alloys thereof and optionally insulation materials are deposited on the under layer according to a sputtering method, a vapor deposition method or another appropriate method to form a 1 to 10 μm thick layer. The electrode formation can be carried out by a screen printing method employing a conductive paste in which fine metal particles are mixed with a low melting point glass, a dipping method or a melt splaying method.

Further, a given voltage is applied across electrodes formed on both sides of a piezoelectric body film to polarize the piezoelectric body film, thereby obtaining a piezoelectric body element (an ultrasound oscillator).

(Ultrasound Probe)

The ultrasound probe of the invention is a probe for a medical ultrasound diagnostic system or a nondestructive ultrasound test system each comprising an oscillator for ultrasound transmission and an oscillator for ultrasound reception. In the invention, it is preferred that one oscillator is constructed so that both of ultrasound transmission and reception is carried out. An ultrasound oscillator for both transmission and reception is constructed employing the piezoelectric body of the invention.

The ultrasound oscillator employing the piezoelectric body of the invention has a broad bandwidth, and is preferably an oscillator capable of carrying out both transmission and reception of ultrasound simultaneously. On account of the broad bandwidth, the ultrasound oscillator has excellent separation of a higher order harmonic wave and enhances sensitivity.

As the preferred embodiment of the invention, the piezoelectric body may be provided on an electrode as a support which has been provided. It is preferred that the thickness matches a preferable reception frequency band region in view of design of the probe. The thickness is preferably from 10 to 800 μm in view of a medical ultrasound diagnostic system for practical use or actual frequency band used for collection of living body information.

The probe may be provided with a backing layer, an acoustic matching layer, an acoustic lens and the like. The probe may be one in which many oscillators having a piezoelectric material are two dimensionally arranged. A plurality of probes, being two dimensionally arranged, may constitute a scanner in which the probes conduct scanning in order, followed by imaging.

The ultrasound probe of the invention may be one comprising an oscillator for ultrasound transmission and an oscillator for ultrasound reception. An oscillator for ultrasound transmission and an oscillator for ultrasound reception can be separately provided in the ultrasound probe.

It is preferred that an oscillator for ultrasound reception comprises the piezoelectric body of the invention. However, well known various inorganic or organic piezoelectric materials can be employed for an oscillator for ultrasound transmission.

Examples of the inorganic piezoelectric materials include quartz, lithium niobate ($LiNbO_3$), potassium niobate tantalate [$K(Ta, Nb)O_3$], barium titanate, ($BaTiO_3$), lithium tantalate ($LiTaO_3$), lead titanate zirconate (PZT), strontium titanate ($SrTiO_3$) and barium strontium titanate (BST). PZT is preferably $Pb(Zr_{1-n}Ti_n)O_3$ ($0.47 \leq n \leq 1$).

An organic piezoelectric film composed of a polymeric material such as polyvinylidene fluoride or the like as an organic piezoelectric material can be employed. The relative dielectric constant in the thickness resonance frequency is preferably from 5 to 50. The relative dielectric constant can be controlled by adjustment of the number of a polar functional group such as a $CF_2$ group or a CN group, composition or a polymerization degree or by polarization treatment as described above.

The organic piezoelectric body film constituting the oscillator for reception of the invention can be a laminate in which a plurality of polymeric materials are multi-layered. In addition to the polymeric materials described above, polymeric materials having a comparatively low relative dielectric constant as described later can be used in combination as polymeric materials to be multi-layered.

In the following examples, the figures in the parentheses represent a relative dielectric constant of the polymeric materials (resins).

Examples of the polymeric materials include methyl methacrylate resin (3.0), acrylonitrile resin (4.0), acetate resin (3.4), aniline resin (3.5), aniline formaldehyde resin (4.0), aminoalkyl resin (4.0), alkyd resin (5.0), nylon 6-6 (3.4), ethylene resin (2.2), epoxy resin (2.5), vinyl chloride resin (3.3), vinylidene chloride resin (3.0), urea formaldehyde resin (7.0), polyacetal resin (3.6), polyurethane (5.0), polyester resin (2.8), polyethylene (low pressure) (2.3), polyethylene terephthalate (2.9), polycarbonate resin (2.9), melamine resin (5.1), melamine formaldehyde resin (8.0), cellulose acetate (3.2), vinyl acetate resin (2.7), styrene resin (2.3), styrene butadiene rubber (3.9), styrol resin (2.4) and ethylene fluoride resin (2.0).

(Medical Ultrasound Diagnostic System)

The above ultrasound probe (transducer) of the invention can be applied to various ultrasound diagnostic systems. For example, it can be suitably applied to an ultrasound medical diagnostic system as shown in FIGS. 1 and 2.

Figure 1:
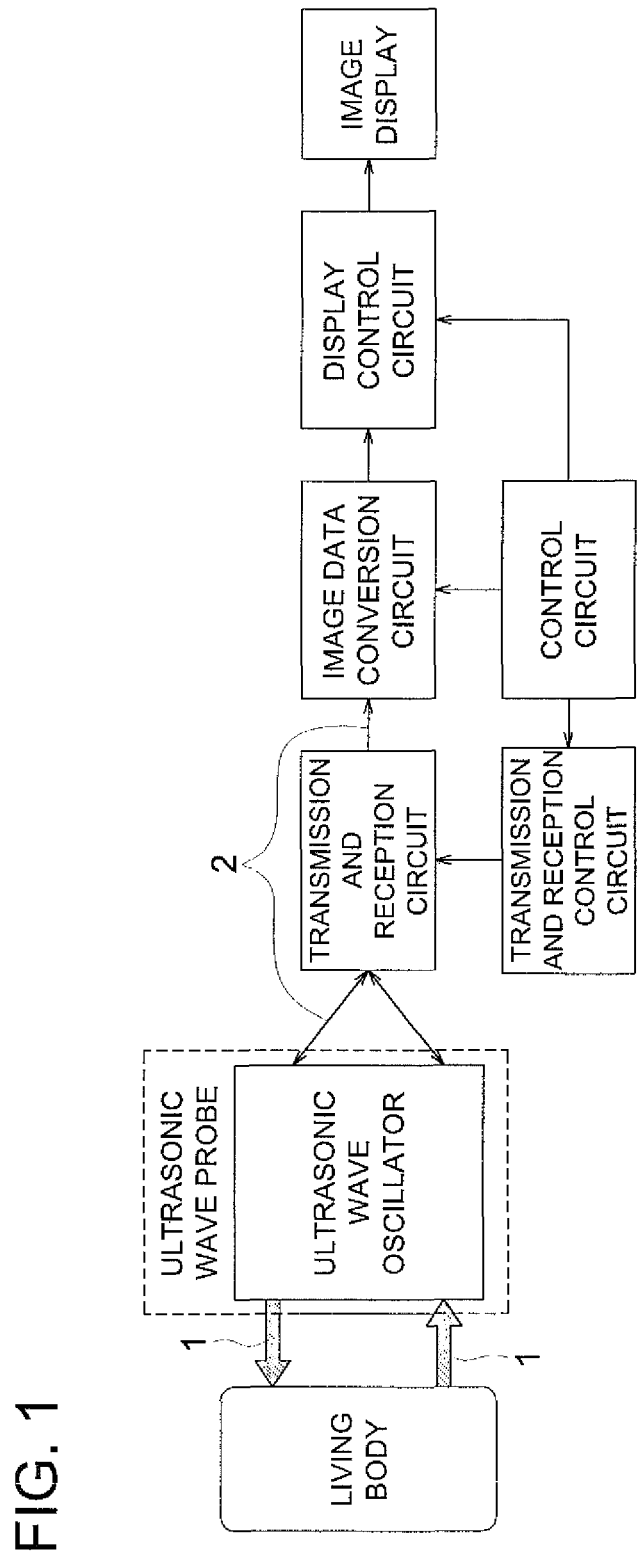
FIG. 1 is a block diagram showing the structure of the main section of an embodiment of the medical ultrasound diagnostic system of the invention.
Figure 2:
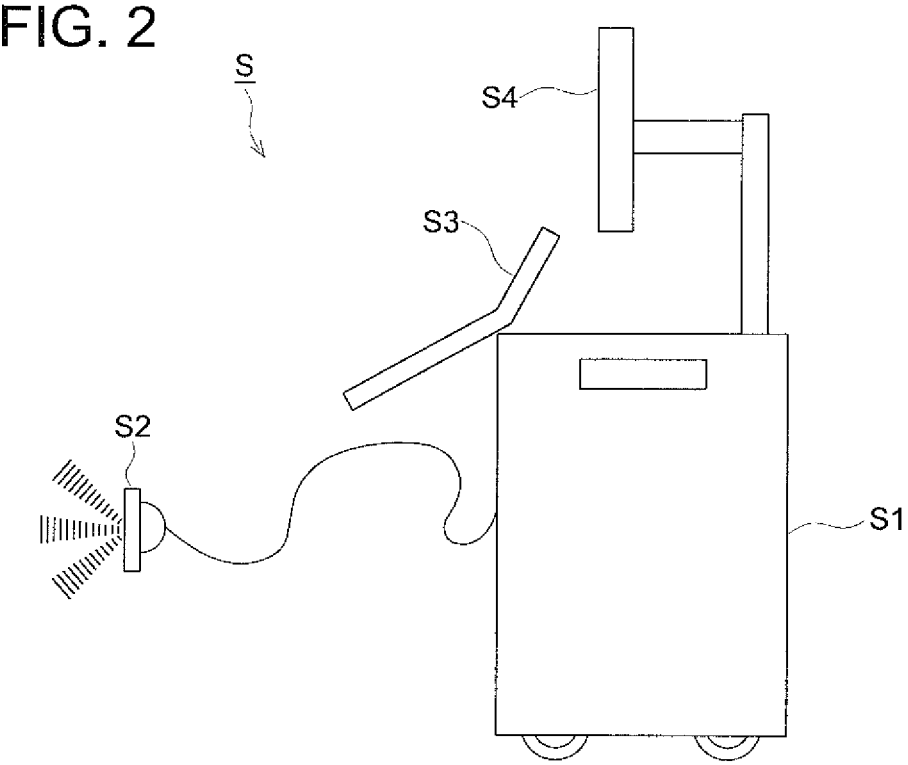
FIG. 2 is an external constitutional diagram of a medical ultrasound diagnostic system.

FIG. 1 is a block diagram showing the structure of the main section of an embodiment of the medical ultrasound diagnostic system of the invention. The medical ultrasound diagnostic system is equipped with an ultrasound probe (transducer) in which a piezoelectric body oscillator is arranged which transmits an ultrasound 1 to an examinee such as a patient and receives an ultrasound 1 reflected from the examinee as an echo signal. The medical ultrasound diagnostic system is further equipped with a transmission and reception circuit having the function, which supplies an electric signal 2 to the ultrasound probe to generate ultrasound, receives an echo signal 2 received by each piezoelectric body oscillator in the ultrasound probe and separates a superposed higher harmonic wave component through a filter, and a transmission and reception control circuit, which controls transmission and reception of the transmission and reception circuit.

The system is equipped with a display control circuit, which controls a monitor with an ultrasound image data converted by the image data conversion circuit and displays an image, and a control circuit, which controls the whole of the medical ultrasound diagnostic system.

The transmission and reception control circuit, the image data conversion circuit and the display control circuit are connected to the control circuit and the operation thereof is controlled through the control circuit. An electric signal is applied to each piezoelectric body oscillator in the ultrasound probe to transmit an ultrasound to an examinee and a reflection wave generated by acoustic impedance mismatch inside the examinee is received by the ultrasound probe.

The ultrasound diagnostic system as described above, comprising the ultrasound oscillator (ultrasound transducer) of the invention which is excellent in piezoelectric characteristic and thermal resistance and which is suitable for high frequency and broad bandwidth, can provide an ultrasound image with improved image quality and reproduction stability as compared with a conventional one.

FIG. 2 is an external constitutional diagram of a medical ultrasound diagnostic system S, comprising a body of medical ultrasound diagnostic system S1, an ultrasound probe S2, an operation input unit S3 and a display unit S4.

(Nondestructive Ultrasound Test System)

The nondestructive ultrasound test system has a constitution principally similar to the medical ultrasound diagnostic system, and can be employed for nondestructive testing for various materials, for example, non nondestructive testing (product test) such as detection of flaws at the welded part of a steel frame or the like according to ultrasound inspection.

Figure 3:
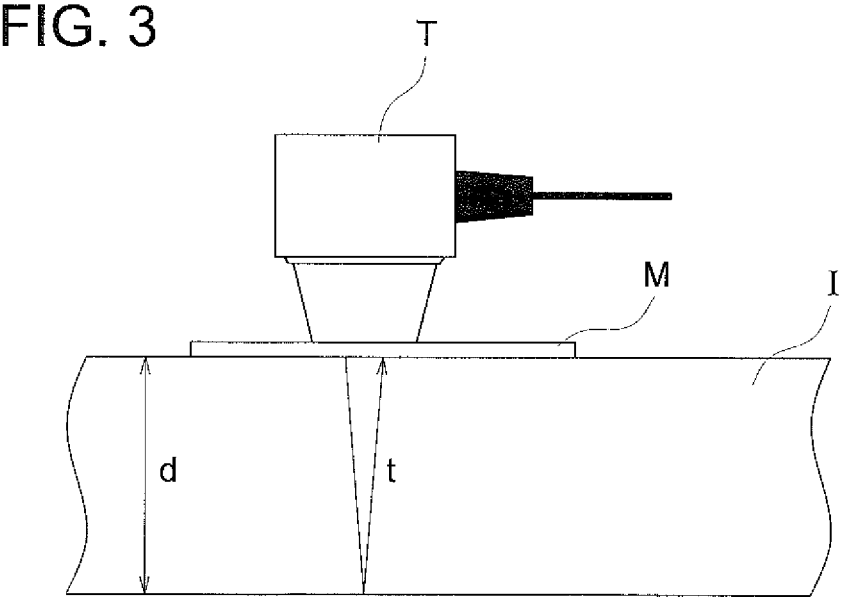
FIG. 3 shows one example of an ultrasound thickness meter as one embodiment of a nondestructive ultrasound test system.

FIG. 3 shows one example of an ultrasound thickness meter as one embodiment of a nondestructive ultrasound test system. A slight amount of liquid as a contact medium (M) is applied onto the surface of an object (I) to be examined, and brought into contact with a transducer (T) to transmit an ultrasound from the contact surface and receive an ultrasound reflected from the opposite surface of the object. The thickness d of the object can be measured based on the ultrasound travel time t taken from the transmission of the ultrasound to the reception of the reflected ultrasound. Because the sonic speed differs due to material of an object to be examined, the sonic speed is adjusted employing a test sample for calibration, whereby correct thickness of the object can be obtained nondestructively.

EXAMPLES

Next, the present invention will be explained referring to examples, but the invention is not specifically limited thereto.

Example 1

Hydrobromic acid was dropwise added to a dimethylformamide (DMF) solution of 4-(1-naphthyl)butylamine and stirred at room temperature to obtain a reaction mixture. Acetone was added to the resulting reaction mixture to precipitate an organic ammonium salt (G1Br). The precipitated organic ammonium salt (G1Br) was isolated by filtration. Lead bromide (PbBr$_2$) was added in a stoichiometrically equivalent amount to a DMF solution of the organic ammonium salt, and stirred at room temperature to produce G1$_2$PbBr$_4$ in the DMF solution. Since the produced G1$_2$PbBr$_4$ had a sufficient purity, the resulting DMF solution was spin coated on a glass plate and dried under vacuum to remove the solvent, thereby forming a piezoelectric body precursor film with a thickness of 2 μm.

This precursor film was subjected to application of a direct current of 100 V through a gold electrode at room temperature. Thus, a piezoelectric body with a d$_{33}$ of 640 pC/N and a −6 db bandwidth of 120% was prepared.

Employing a medical ultrasound diagnostic system to which an ultrasound transducer with the piezoelectric body was connected, a phantom was scanned. An echo from a target depth of 15 cm was received at a transmission ultrasound frequency of 6 MHz and an image with a spatial resolution of 0.1 mm was obtained.

Example 2

6-(2-bicyclo-2,2,1-heptyl)-hexyl benzyl sulfoxide and 3-p-tolylpropyl magnesium iodide were refluxed in ether for 2 hours and then added with hydrobromic acid to obtain a sulfonium salt (G2I: bis(2-bicyclo-2,2,1-heptyl)-(3-p-tolylpropyl) sulfonium iodide). The resulting sulfonium salt was dissolved in dimethyl sulfoxide, added with lead iodide in a stoichiometrically equivalent amount and then stirred at room temperature. Acetone was added to the resulting dimethyl sulfoxide solution to precipitate G2$_2$PbI$_4$. Subsequently, a DMF solution of G2$_2$PbI$_4$ was provided and cast on a glass plate and dried under vacuum to remove the solvent, thereby forming a piezoelectric body precursor film with a thickness of 10 μm. This precursor film was subjected to application of a direct current of 1 kV through a gold electrode at room temperature. Thus, a piezoelectric body with 1040 pC/N of d$_{33}$ and 105% of a −6 db bandwidth was prepared.

Employing a medical ultrasound diagnostic system to which an ultrasound transducer with the piezoelectric body was connected, a phantom was scanned. An echo from a target depth of 4 cm was received at a transmission ultrasound frequency of 18 MHz and an image with a spatial resolution of 0.06 mm was obtained.

Example 3

Hydroiodic acid was dropwise added to a dimethylformamide (DMF) solution of N-vinylcarbazole and stirred at room temperature to obtain a reaction mixture. Methanol was added to the resulting reaction mixture to precipitate an organic ammonium salt (G3). The precipitated organic ammonium salt (G3) was isolated by filtration. Cadmium iodide was added in a stoichiometrically equivalent amount to a DMF solution of the organic ammonium salt, and stirred at room temperature. Acetone was added to the resulting DMF solution to precipitate G3$_2$CdI4. Subsequently, the precipitated G3$_2$CdI$_4$ was dissolved in DMF and the DMF solution of G3$_2$CdI$_4$ was dip coated on a glass plate and dried under vacuum to remove the solvent, thereby forming a piezoelectric body precursor film with a thickness of 20 μm. The precursor film was subjected to ultraviolet ray irradiation under argon atmosphere through a high pressure mercury lamp and then to application of a direct current of 2 kV through a gold electrode at room temperature. Thus, a piezoelectric body with a d$_{33}$ of 760 pC/N and a −6 db bandwidth of 160% was prepared.

Employing a nondestructive ultrasound test system to which an ultrasound transducer with the piezoelectric body was connected, a steel frame was scanned. An echo corresponding to a third higher harmonic wave (30 MHz) was received from a depth of 4 cm at a transmission ultrasound frequency of 10 MHz, and a crack of 0.2 mm was detected.

Example 4

2-Methoxyethanol (7.5 ml) solution of lead acetate trihydrate (3.8 g) was refluxed at 120° C. for 12 hours, cooled to 90° C., then added with titanium tetraisopropoxide (2.2 g) and zirconium tetrapropoxide (0.82 g), and further refluxed at 140° C. for 6 hours. Subsequently, the resulting reaction solution was added with a toluene (5 ml) solution of C60 (7.2 mg) and 5 ml of a mixture of 2-methoxyethanol (50 parts by volume) with acetic acid (50 parts by volume), and stirred at 80° C. for one hour. The resulting reaction mixture was dip coated on a silicon substrate and air dried at room temperature for two hours. The coated film on the substrate was calcined at a temperature of from 70 to 120° C. for four hours and further at 350° C. for thirty minutes in air, and further calcined at 550° C. for two hours and further at a temperature of from 900 to 1200° C. for four hours under an argon atmosphere having an oxygen concentration of not more than 5 ppm. Thus, a piezoelectric body precursor film in the invention with a thickness of 4 μm, formed on the silicon substrate, was prepared.

After a gold electrode was vapor deposited onto the precursor film, the resulting film was subjected to application of a direct current of 200 V through a gold electrode at room temperature. Thus, an inventive piezoelectric body with a $d_{33}$ of 450 pCN and a −6 db bandwidth of 120% was prepared. When this piezoelectric body was observed employing an ultra low accelerating voltage scanning electron microscope equipped with a dispersion type X ray spectrometer, it proved that carbons with a uniform size, having a particle size of from 5 to 40 mm and an average particle size of 30 nm, were dispersed. Employing a medical ultrasound diagnostic system to which an ultrasound transducer with the piezoelectric body was connected, a phantom was scanned. An echo from a target depth of 16 cm was received at a transmission ultrasound frequency of 6 MHz and an image with a spatial resolution of 0.1 mm was obtained.

Example 5

A 2-methoxyethanol (22.5 ml) solution of lead acetate trihydrate (11.4 g) was refluxed at 120° C. for 12 hours, cooled to 90° C., and then added with magnesium ethoxide (038 g), niobium (V) ethoxide (2.12 g) and titanium tetraisopropoxide (4.4 g). The resulting solution was placed in an autoclave the inside of which was substituted with argon, and stirred at 110° C. for 16 hours. Subsequently, the resulting reaction solution was added with a toluene (5 ml) solution of ferrocene (6.5 mg) and 2-methoxyethanol (10 ml), and stirred at 60° C. for one hour. The resulting reaction mixture was spin coated on a tungsten carbide substrate and air dried at room temperature for around two hours. The coated film on the substrate was heat treated in air at 100° C. for three hours and then at 1050° C. for four hours. The resulting heat treated product was heated to 1600° C. under a stream of a hydrogen gas and a toluene vapor. Thus, a composite film, in which carbon nanotubes grew, was obtained. Subsequently, the composite film was calcined at 3000° C. for one minute under an argon atmosphere having an oxygen concentration of not more than 5 ppm. Thus, an inventive piezoelectric body precursor film with a thickness of 10 μm, formed on the tungsten carbide substrate, was prepared.

After a gold electrode was vapor deposited onto the precursor film, the resulting film was subjected to application of a direct current of 500 V through a gold electrode at room temperature. Thus, an inventive piezoelectric body with a $d_{33}$ of 1060 pC/N and a −6 db bandwidth of 150% was prepared. When this piezoelectric body was observed employing an ultra low accelerating voltage scanning electron microscope equipped with a dispersion type X ray spectrometer, it proved that carbons with a uniform size, which have a particle size of from 20 to 60 nm and an average particle size of 50 nm were dispersed. Employing a medical ultrasound diagnostic system to which an ultrasound transducer with the piezoelectric body was connected, a phantom was scanned. An echo from a target depth of 4 cm was received at a transmission ultrasound frequency of 18 MHz and an image with a spatial resolution of 0.06 mm was obtained.

Example 6

A bulk mixture of $Pb(Zn_{1/3}Nb_{2/3})O_3$ (6.4 g) and $PbTiO_3$ (7.4 g) was dispersed in a mixture solvent (50 ml) of toluene (30 ml) and isopropyl alcohol (20 ml), and dispersed in a ball mill to obtain a slurry. To the slurry was added one milliliter of a toluene (10 ml) solution of multi-wall carbon nanotubes (2.7 mg) with an average diameter of 45 nm and an average length of 60 μm and vinyl butyral-vinyl alcohol-vinyl acetate copolymer (1 mg) with a weight average molecular weight of from 50000 to 80000, and stirred. The resulting mixture dispersion solution was jetted from a diamond nozzle having an outlet with a diameter of 4 μm at a pressure of 150 MPa so that a mixture of the perovskite and the multi-wall carbon nanotubes was further dispersed. The process in which the dispersion solution was jetted from the diamond nozzle was repeated ten times. Then, the resulting dispersion solution was dip coated on a silicon substrate, dried to remove the solvent, and then calcined at 1200° C. under an argon atmosphere. Thus, an inventive piezoelectric body precursor film with a thickness of 10 μm was prepared. The precursor film was subjected to polarization treatment according to corona discharge generated in air by application of a direct current of 5 kV at a distance between a needle electrode and the ground being 5 cm. Thus, an inventive piezoelectric body with a $d_{33}$ of 940 pC/N and a −6 db bandwidth of 130% was prepared. When this piezoelectric body was observed employing an ultra low accelerating voltage scanning electron microscope equipped with a dispersion type X ray spectrometer, it proved that carbons with a uniform size were dispersed in the piezoelectric body, the carbons having a particle size of from 60 to 240 nm and an average particle size of 200 nm. Employing a nondestructive ultrasound test system to which an ultrasound transducer with this piezoelectric body was connected, a steel frame was scanned. An echo corresponding to a third higher harmonic wave (30 MHz) was received from a depth of 4 cm at a transmission ultrasound frequency of 10 MHz, and a crack of 0.2 mm was detected.

Comparative Example 1

A mixture of 540 mg of polyurea obtained from 1,4-diaminobenzene and xylylene diisocyanate, 3.9 g of tris(acryloxy)cyanurate, 2 mg of 4-hydroxycyclohexyl phenyl ketone and 46 ml of DMF was stirred at room temperature to obtain a uniform solution. The resulting solution was spin coated on a substrate and dried at 60° C. under a reduced pressure of 10 Pa to remove DMF, thereby obtaining a film with a thickness of 36 μm. The resulting film was irradiated with a 310 nm wavelength light at 0.8 J through a high pressure mercury lamp while stretching by a factor of 400%, thereby obtaining a film with a thickness of 14 μm. This film had a −6 db bandwidth of 240%, exhibiting a relatively broad bandwidth, however, the film had a $d_{33}$ of 5 pC/N, exhibiting a low piezoelectricity.

Employing a medical ultrasound diagnostic system to which an ultrasound transducer with this piezoelectric body was connected, a phantom was scanned, and an echo from a target depth of 16 cm was received at a transmission ultrasound frequency of 6 MHz and an image with a spatial resolution of 2 mm was obtained.

Comparative Example 2

A nickel mold, on the surface of which prisms with a size of 25 μm×25 μm×250 μm were arranged at a pitch of 50 μm, was prepared according to a microfabrication process employing a synchrotron radiation with a wavelength of 3A and polymethyl methacrylate (PMMA) as a resist A melted PMMA was cast in the resulting nickel mold, and cooled to obtain a PMMA mold having the concave and convex configuration corresponding to that of the nickel mold. Subsequently, a polyvinyl alcohol slurry containing PZT having a particle size of 0.4 μm in an amount of 60% by volume was cast in the resulting PMMA mold, and then the PMMA was removed by ionic etching due to oxygen plasma, followed by calcination at 1200° C. Thus, a prism structure was prepared in which PZT prisms having a size of 22 mm×22 mm×220 mm were aligned. A bisphenol A type resin was cast in the resulting prism structure and cured to obtain a 1-3 composite as an objective product. This composite had a −6 db bandwidth of 140%, exhibiting a relatively broad bandwidth, however, the composite had a $d_{33}$ of 46 pC/N, exhibiting a low piezoelectricity. This piezoelectricity of the composite was proved to be extremely low as compared with that of a pure PZT.

Employing a nondestructive ultrasound test system to which an ultrasound transducer with this piezoelectric body, was connected, a steel frame was scanned, however, no echo reception signal was detected from a depth of 4 cm at a transmission ultrasound frequency of 10 MHz.

Comparative Example 3

A C60 saturated toluene solution of 150 ml, 50 ml of dimethanol amine, and 100 ml of acetic acid were added to a uniform dispersion solution comprised of 10.93 g of zirconium tetra-n-propoxide, 5.50 g of titanium tetraisopropoxide, 16.69 g of lead acetate trihydrate and 100 ml of isopropyl alcohol to prepare a composite precursor dispersion solution. The resulting precursor dispersion solution was dip coated on a silicon substrate, heated in air while the temperature was elevated from 25° C. at a temperature raising speed of 50° C./minute for 10 minutes, and then further heated at a constant temperature of 525° C. for additional 10 minutes to obtain a composite film. This composite film had a −6 dB bandwidth of 90%, exhibiting a narrow bandwidth, and had a $d_{33}$ of 46 pC/N, exhibiting a low piezoelectricity. The piezoelectricity of the composite film was extremely low as compared with that of a pure PZT. When this piezoelectric body was observed employing an ultra low accelerating voltage scanning electron microscope equipped with a dispersion type X ray spectrometer, it proved that carbons with an average particle size of 350 nm and a particle size of from 260 to 3000 nm were dispersed in the piezoelectric body. Employing a medical ultrasound diagnostic system to which an ultrasound transducer with this piezoelectric body was connected, a phantom was scanned. An echo from a target depth of 10 cm was received at a transmission ultrasound frequency of 4 MHz and an image with a poor spatial resolution of 4 mm was obtained.

It is apparent that as compared with the piezoelectric bodies prepared in the comparative examples above or a conventional piezoelectric body, the inventive piezoelectric bodies prepared in the examples above are excellent in view of a piezoelectric strain constant $d_{33}$, and a −6 dB bandwidth, and further in view of a broad bandwidth applicable and a high detection sensitivity an ultrasound echo observed, when the piezoelectric bodies are employed in an ultrasound transducer. Accordingly, the piezoelectric body of the invention can be suitably applied to a sensor, an actuator, an ultrasound transducer, or a medical ultrasound diagnostic system or a nondestructive ultrasound test system employing them.

EXPLANATION OF THE SYMBOLS

1. Sonic wave
2. Electric signal
S. Medical ultrasound diagnostic system
S1. Body of medical ultrasound diagnostic system
S2. Ultrasound probe
S3. Operation input section
S4. Display section

The invention claimed is:

1. A piezoelectric body comprising a laminate structure represented by the following general formula in which an organic onium G and an inorganic phase $MX_4$ are alternately superposed on each other in the form of layers, General formula,

$$G_2MX_4$$

wherein G represents an organic onium, M represents an element of Group IV or a transition metal, and X represents Cl, Br or I.

2. The piezoelectric body of claim 1, wherein in the general formula, the organic onium is an organic ammonium, an organic phosphonium, an organic sulfonium or an organic oxonium.

3. The piezoelectric body of claim 1, wherein in the general formula, the M is Cd, Cu, Fe, Mn, Pd or Pb.

4. The piezoelectric body of claim 1, wherein the laminate structure is an organic perovskite in the form of layers.

5. An ultrasound transducer comprising the piezoelectric body of claim 1.

6. A medical ultrasound diagnostic system comprising the ultrasound transducer of claim 5.

7. A nondestructive ultrasound test system comprising the ultrasound transducer of claim 5.

* * * * *